(12) United States Patent
Poellinger et al.

(10) Patent No.: US 7,098,376 B2
(45) Date of Patent: Aug. 29, 2006

(54) TRANSGENIC MOUSE EXPRESSING CONSTITUTIVELY ACTIVE HYDROCARBON RECEPTOR

(75) Inventors: Lorenz Poellinger, Stockholm (SE); Jaqueline McGuire, Huddinge (SE); Annika Hanberg Wiklund, Stocksund (SE); Patrik Andersson, Stockholm (SE)

(73) Assignee: InDex Pharmaceuticals AB, Stockholm (SE)

( * ) Notice: Subject to any disclaimer, the term of this patent is extended or adjusted under 35 U.S.C. 154(b) by 0 days.

(21) Appl. No.: 10/415,255

(22) PCT Filed: Oct. 25, 2001

(86) PCT No.: PCT/SE01/02335

§ 371 (c)(1),
(2), (4) Date: Oct. 30, 2003

(87) PCT Pub. No.: WO02/34928

PCT Pub. Date: May 2, 2002

(65) Prior Publication Data

US 2004/0088743 A1    May 6, 2004

Related U.S. Application Data

(60) Provisional application No. 60/243,548, filed on Oct. 26, 2000.

(51) Int. Cl.
| | |
|---|---|
| *A01K 67/027* | (2006.01) |
| *A01K 67/00* | (2006.01) |
| *A01K 67/033* | (2006.01) |
| *C12N 15/00* | (2006.01) |
| *C12N 15/63* | (2006.01) |
| *C12N 15/85* | (2006.01) |
| *C12N 15/87* | (2006.01) |
| *C12N 5/02* | (2006.01) |
| *C12N 5/00* | (2006.01) |

(52) U.S. Cl. ............................. 800/18; 800/8; 800/14; 800/21; 800/24; 435/455; 435/325

(58) Field of Classification Search .................... 800/3, 800/18, 21, 22, 25, 8, 14, 24; 435/455, 463, 435/320.1, 325
See application file for complete search history.

(56) References Cited

U.S. PATENT DOCUMENTS

| 5,378,822 A | 1/1995 | Bradfield et al. .......... 536/23.5 |
| 5,650,283 A | 7/1997 | Bradfield et al. ............ 435/7.1 |

FOREIGN PATENT DOCUMENTS

WO        WO 99/28464        6/1999

OTHER PUBLICATIONS

Kappell et al. Current Opinion in Biotechnology 3:548-553 (1992).*
Mullins et al. Hypertension 22:630-633 (1993).*
Houdebine. J. Biotech. 34:269-287 (1994).*
Mullins et al. J. Clin. Invest. 98:S37-S40 (1996).*
Cameron. Molec. Biol. 7:253-265 (1997).*
Sigmund. Arterioscler. Throm. Vasc. Biol. 20:1425-1429 (2000).*
Niemann. Transg. Res. 7:73-75 (1998).*
Andersson et al. Organohalogen Compounds, 37:89-91 (1998).*
Charreau et al. Transgenic Research, 5:223-234 (1996).*
Breast Cancer Researcy and Treatment, Anthony Trombino et al, Expression of the aryl hydrocarbon receptor/transcription factor (AhR) and AhR-regulated CYPI gene transcrips in a ragt module mammary.

* cited by examiner

Primary Examiner—Anne-Marie Falk
Assistant Examiner—Thaian N. Ton
(74) Attorney, Agent, or Firm—Young & Thompson

(57) ABSTRACT

The present invention makes available powerful tools for the study of cancer, based on a novel expression construct for a constitutively active hydrocarbon receptor CA-AhR. The invention further comprises transgenic non-human animals, preferably mammals, expressing CA-AhR in one or more tissues thereof. An animal model based on the transgenic non-human animals forms the basis for novel methods e.g. for the study of cancer; for the screening of compounds, such as drug candidates; for the investigation of the molecular mechanisms of cancer, in particular stomach cancer; for the investigation of the mechanisms of highly differentiated adenocarcinoma etc. Likewise, in vitro models based on transformed cells or cell lines, functionally incorporating the inventive construct are disclosed.

5 Claims, 7 Drawing Sheets

SEQUENCE LISTING

<160> NUMBER OF SEQ ID NOS: 4

<210> SEQ ID NO 1
<211> LENGTH: 2418
<212> TYPE: DNA
<213> ORGANISM: Mus musculus
<220> FEATURE:
<221> NAME/KEY: CDS
<222> LOCATION: (1)..(2415)

<400> SEQUENCE: 1

```
atg agc agc ggc gcc aac atc acc tat gcc agc cgc aag cgg cgc aag      48
Met Ser Ser Gly Ala Asn Ile Thr Tyr Ala Ser Arg Lys Arg Arg Lys
 1               5                  10                  15
```

```
ccg gtg cag aaa aca gta aag ccc atc ccc gct gaa gga att aag tca        96
Pro Val Gln Lys Thr Val Lys Pro Ile Pro Ala Glu Gly Ile Lys Ser
         20                  25                  30 aat cct tct aag cga cac aga gac cgg ctg aac aca gag tta gac cgc       144
Asn Pro Ser Lys Arg His Arg Asp Arg Leu Asn Thr Glu Leu Asp Arg
     35                  40                  45 ctg gcc agc ctg ctg ccc ttc ccg caa gat gtt att aat aag ctg gac       192
Leu Ala Ser Leu Leu Pro Phe Pro Gln Asp Val Ile Asn Lys Leu Asp
 50                  55                  60 aaa ctc tct gtt ctt agg ctc agc gtc acg tac ctg agg gcc aag agc       240
Lys Leu Ser Val Leu Arg Leu Ser Val Thr Tyr Leu Arg Ala Lys Ser
 65                  70                  75                  80 ttc ttt gat gtt gca tta aag tcc acc cct gct gac aga aat gga ggc       288
Phe Phe Asp Val Ala Leu Lys Ser Thr Pro Ala Asp Arg Asn Gly Gly
             85                  90                  95 cag gac cag tgt aga gca caa atc aga gac tgg cag gat ttg caa gaa       336
Gln Asp Gln Cys Arg Ala Gln Ile Arg Asp Trp Gln Asp Leu Gln Glu
                100                 105                 110 gga gag ttc ttg tta cag gcg ctg aat ggc ttt gtg ctg gtt gtc aca       384
Gly Glu Phe Leu Leu Gln Ala Leu Asn Gly Phe Val Leu Val Val Thr
            115                 120                 125 gca gat gcc ttg gtc ttc tat gct tcc tcc act atc caa gat tac ctg       432
Ala Asp Ala Leu Val Phe Tyr Ala Ser Ser Thr Ile Gln Asp Tyr Leu
130                 135                 140 ggc ttt cag cag tct gat gtc atc cat cag agc gta tat gag ctc atc       480
Gly Phe Gln Gln Ser Asp Val Ile His Gln Ser Val Tyr Glu Leu Ile
145                 150                 155                 160 cat aca gaa gac cgg gcg gaa ttc cag cgc cag ctt cac tgg gct cta       528
His Thr Glu Asp Arg Ala Glu Phe Gln Arg Gln Leu His Trp Ala Leu
                165                 170                 175 aac cca gac tct gca caa gga gtg gac gaa gcc cat ggc cct cca cag       576
Asn Pro Asp Ser Ala Gln Gly Val Asp Glu Ala His Gly Pro Pro Gln
            180                 185                 190 gca gca gtc tat tat acc cca gac cag ctt cct cca gag aac gct tct       624
Ala Ala Val Tyr Tyr Thr Pro Asp Gln Leu Pro Pro Glu Asn Ala Ser
        195                 200                 205 ttc atg gag agg tgc ttc agg tgc cgg ctg agg tgc ctg ctg gat aat       672
Phe Met Glu Arg Cys Phe Arg Cys Arg Leu Arg Cys Leu Leu Asp Asn
    210                 215                 220 tca tct ggt ttt ctg gca atg aat ttc caa ggg agg tta aag tat ctt       720
Ser Ser Gly Phe Leu Ala Met Asn Phe Gln Gly Arg Leu Lys Tyr Leu
225                 230                 235                 240 cat gga cag aac aag aaa ggg aag gac gga gcg ctg ctt cct cca caa       768
His Gly Gln Asn Lys Lys Gly Lys Asp Gly Ala Leu Leu Pro Pro Gln
                245                 250                 255 ctg gct ttg ttt gca ata gct act cca ctt cag cca ccc tcc atc ctg       816
Leu Ala Leu Phe Ala Ile Ala Thr Pro Leu Gln Pro Pro Ser Ile Leu
            260                 265                 270 gaa att cga acc aaa aac ttc atc ttc agg acc aaa cac aag cta gac       864
Glu Ile Arg Thr Lys Asn Phe Ile Phe Arg Thr Lys His Lys Leu Asp
        275                 280                 285 ttc aca cct att ggt tgt gat gcc aaa ggg cag ctt att ctg ggc tat       912
Phe Thr Pro Ile Gly Cys Asp Ala Lys Gly Gln Leu Ile Leu Gly Tyr
    290                 295                 300 aca gaa gta gag ctg tgc aca aga gga tcg ggg tac cag ttc atc cat       960
Thr Glu Val Glu Leu Cys Thr Arg Gly Ser Gly Tyr Gln Phe Ile His
305                 310                 315                 320 gct gca gac ata ctt cac tgt gca gaa tcc cac atc cgc atg att aag      1008
Ala Ala Asp Ile Leu His Cys Ala Glu Ser His Ile Arg Met Ile Lys
                325                 330                 335
```

```
act gga gaa agt ggc atg aca gtt ttc cgg ctt ctt gca aaa cac agt    1056
Thr Gly Glu Ser Gly Met Thr Val Phe Arg Leu Leu Ala Lys His Ser
            340                 345                 350 cgc tgg agg tgg gtc cag tcc aat gca cgc ttg att tac aga aat gga    1104
Arg Trp Arg Trp Val Gln Ser Asn Ala Arg Leu Ile Tyr Arg Asn Gly
            355                 360                 365 aga cca gat tac atc atc gcc act cag aga cca ctg acg gat gaa gaa    1152
Arg Pro Asp Tyr Ile Ile Ala Thr Gln Arg Pro Leu Thr Asp Glu Glu
        370                 375                 380 gga cga gag cat tta cag aag cga agt acg tcg ctg ccc ttc atg ttt    1200
Gly Arg Glu His Leu Gln Lys Arg Ser Thr Ser Leu Pro Phe Met Phe
385                 390                 395                 400 gct acc gga gag gct gtg ttg tac gag atc tcc agc cct ttc tct ccc    1248
Ala Thr Gly Glu Ala Val Leu Tyr Glu Ile Ser Ser Pro Phe Ser Pro
            405                 410                 415 ata atg gat ccc cta cca ata cgc acc aaa agc aac act agc agg aaa    1296
Ile Met Asp Pro Leu Pro Ile Arg Thr Lys Ser Asn Thr Ser Arg Lys
            420                 425                 430 gac tgg gct ccc cag tca acc cca agt aag gat tct ttc cac ccc agt    1344
Asp Trp Ala Pro Gln Ser Thr Pro Ser Lys Asp Ser Phe His Pro Ser
            435                 440                 445 tct ctt atg agt gcc ctc atc cag cag gat gag tcc atc tat ctg tgt    1392
Ser Leu Met Ser Ala Leu Ile Gln Gln Asp Glu Ser Ile Tyr Leu Cys
450                 455                 460 cct cct tca agc cct gcg ctg tta gac agc cat ttt ctc atg ggc tcc    1440
Pro Pro Ser Ser Pro Ala Leu Leu Asp Ser His Phe Leu Met Gly Ser
465                 470                 475                 480 gtg agc aag tgc ggg agt tgg caa gac agc ttt gcg gcc gca gga agt    1488
Val Ser Lys Cys Gly Ser Trp Gln Asp Ser Phe Ala Ala Ala Gly Ser
            485                 490                 495 gag gct gcg ctg aaa cat gag caa att ggc cat gct cag gac gtg aac    1536
Glu Ala Ala Leu Lys His Glu Gln Ile Gly His Ala Gln Asp Val Asn
            500                 505                 510 ctt gca ctc tct ggc ggc ccc tca gag ctc ttt ccg gat aat aaa aat    1584
Leu Ala Leu Ser Gly Gly Pro Ser Glu Leu Phe Pro Asp Asn Lys Asn
            515                 520                 525 aat gac ttg tac agc atc atg agg aac ctt ggg att gat ttt gaa gat    1632
Asn Asp Leu Tyr Ser Ile Met Arg Asn Leu Gly Ile Asp Phe Glu Asp
        530                 535                 540 atc aga agc atg cag aac gag gag ttc ttc aga act gac tcc acc gct    1680
Ile Arg Ser Met Gln Asn Glu Glu Phe Phe Arg Thr Asp Ser Thr Ala
545                 550                 555                 560 gct ggt gag gtt gac ttc aaa gac atc gac ata acg gac gaa atc ctg    1728
Ala Gly Glu Val Asp Phe Lys Asp Ile Asp Ile Thr Asp Glu Ile Leu
            565                 570                 575 acc tac gtg cag gat tcc ctg aac aat tca act ttg ctg aac tcg gct    1776
Thr Tyr Val Gln Asp Ser Leu Asn Asn Ser Thr Leu Leu Asn Ser Ala
            580                 585                 590 tgc cag cag cag cct gtg act cag cac cta agc tgt atg ctg cag gag    1824
Cys Gln Gln Gln Pro Val Thr Gln His Leu Ser Cys Met Leu Gln Glu
            595                 600                 605 cgc ctg caa cta gag caa cag caa cag ctt cag cag ccc ccg ccg cag    1872
Arg Leu Gln Leu Glu Gln Gln Gln Gln Leu Gln Gln Pro Pro Pro Gln
        610                 615                 620 gct ctg gag ccc cag cag cag ctg tgt cag atg gtg tgc ccc cag caa    1920
Ala Leu Glu Pro Gln Gln Gln Leu Cys Gln Met Val Cys Pro Gln Gln
625                 630                 635                 640 gat ctg ggt ccg aag cac acg caa atc aac ggc acg ttt gca agt tgg    1968
Asp Leu Gly Pro Lys His Thr Gln Ile Asn Gly Thr Phe Ala Ser Trp
```

```
                    645                 650                 655
aac ccc acc cct ccc gtg tct ttc aac tgt ccc cag cag gaa cta aag    2016
Asn Pro Thr Pro Pro Val Ser Phe Asn Cys Pro Gln Gln Glu Leu Lys
            660                 665                 670 cac tat cag ctc ttt tcc agc tta cag ggg act gct cag gaa ttt ccc    2064
His Tyr Gln Leu Phe Ser Ser Leu Gln Gly Thr Ala Gln Glu Phe Pro
            675                 680                 685 tac aaa cca gag gtg gac agt gtg cct tac aca cag aac ttt gct ccc    2112
Tyr Lys Pro Glu Val Asp Ser Val Pro Tyr Thr Gln Asn Phe Ala Pro
            690                 695                 700 tgt aat cag cct ctg ctt cca gaa cat tcc aag agt gtg cag ttg gac    2160
Cys Asn Gln Pro Leu Leu Pro Glu His Ser Lys Ser Val Gln Leu Asp
705                 710                 715                 720 ttc cct gga agg gat ttt gaa ccg tcc ctg cat ccc act act tct aat    2208
Phe Pro Gly Arg Asp Phe Glu Pro Ser Leu His Pro Thr Thr Ser Asn
                725                 730                 735 tta gat ttt gtc agt tgt tta caa gtt cct gaa aac caa agt cat ggg    2256
Leu Asp Phe Val Ser Cys Leu Gln Val Pro Glu Asn Gln Ser His Gly
                740                 745                 750 ata aac tca cag tcc gcc atg gtc agt cct cag gca tac tat gct ggg    2304
Ile Asn Ser Gln Ser Ala Met Val Ser Pro Gln Ala Tyr Tyr Ala Gly
                755                 760                 765 gcc atg tcc atg tat cag tgc cag cca ggg cca cag cgc acc cct gtg    2352
Ala Met Ser Met Tyr Gln Cys Gln Pro Gly Pro Gln Arg Thr Pro Val
770                 775                 780 gac cag acg cag tac agc tct gaa att cca ggt tct cag gca ttc cta    2400
Asp Gln Thr Gln Tyr Ser Ser Glu Ile Pro Gly Ser Gln Ala Phe Leu
785                 790                 795                 800 agc aag gtg cag agt tga                                            2418
Ser Lys Val Gln Ser
                805

<210> SEQ ID NO 2
<211> LENGTH: 805
<212> TYPE: PRT
<213> ORGANISM: Mus musculus

<400> SEQUENCE: 2

Met Ser Ser Gly Ala Asn Ile Thr Tyr Ala Ser Arg Lys Arg Arg Lys
1               5                   10                  15

Pro Val Gln Lys Thr Val Lys Pro Ile Pro Ala Glu Gly Ile Lys Ser
                20                  25                  30

Asn Pro Ser Lys Arg His Arg Asp Arg Leu Asn Thr Glu Leu Asp Arg
            35                  40                  45

Leu Ala Ser Leu Leu Pro Phe Pro Gln Asp Val Ile Asn Lys Leu Asp
        50                  55                  60

Lys Leu Ser Val Leu Arg Leu Ser Val Thr Tyr Leu Arg Ala Lys Ser
65                  70                  75                  80

Phe Phe Asp Val Ala Leu Lys Ser Thr Pro Ala Asp Arg Asn Gly Gly
                85                  90                  95

Gln Asp Gln Cys Arg Ala Gln Ile Arg Asp Trp Gln Asp Leu Gln Glu
            100                 105                 110

Gly Glu Phe Leu Leu Gln Ala Leu Asn Gly Phe Val Leu Val Val Thr
        115                 120                 125

Ala Asp Ala Leu Val Phe Tyr Ala Ser Ser Thr Ile Gln Asp Tyr Leu
    130                 135                 140

Gly Phe Gln Gln Ser Asp Val Ile His Gln Ser Val Tyr Glu Leu Ile
145                 150                 155                 160
```

-continued

```
His Thr Glu Asp Arg Ala Glu Phe Gln Arg Gln Leu His Trp Ala Leu
            165                 170                 175

Asn Pro Asp Ser Ala Gln Gly Val Asp Glu Ala His Gly Pro Pro Gln
            180                 185                 190

Ala Ala Val Tyr Tyr Thr Pro Asp Gln Leu Pro Pro Glu Asn Ala Ser
            195                 200                 205

Phe Met Glu Arg Cys Phe Arg Cys Arg Leu Arg Cys Leu Leu Asp Asn
            210                 215                 220

Ser Ser Gly Phe Leu Ala Met Asn Phe Gln Gly Arg Leu Lys Tyr Leu
225                 230                 235                 240

His Gly Gln Asn Lys Lys Gly Lys Asp Gly Ala Leu Leu Pro Pro Gln
            245                 250                 255

Leu Ala Leu Phe Ala Ile Ala Thr Pro Leu Gln Pro Pro Ser Ile Leu
            260                 265                 270

Glu Ile Arg Thr Lys Asn Phe Ile Phe Arg Thr Lys His Lys Leu Asp
            275                 280                 285

Phe Thr Pro Ile Gly Cys Asp Ala Lys Gly Gln Leu Ile Leu Gly Tyr
            290                 295                 300

Thr Glu Val Glu Leu Cys Thr Arg Gly Ser Gly Tyr Gln Phe Ile His
305                 310                 315                 320

Ala Ala Asp Ile Leu His Cys Ala Glu Ser His Ile Arg Met Ile Lys
            325                 330                 335

Thr Gly Glu Ser Gly Met Thr Val Phe Arg Leu Leu Ala Lys His Ser
            340                 345                 350

Arg Trp Arg Trp Val Gln Ser Asn Ala Arg Leu Ile Tyr Arg Asn Gly
            355                 360                 365

Arg Pro Asp Tyr Ile Ile Ala Thr Gln Arg Pro Leu Thr Asp Glu Glu
            370                 375                 380

Gly Arg Glu His Leu Gln Lys Arg Ser Thr Ser Leu Pro Phe Met Phe
385                 390                 395                 400

Ala Thr Gly Glu Ala Val Leu Tyr Glu Ile Ser Ser Pro Phe Ser Pro
            405                 410                 415

Ile Met Asp Pro Leu Pro Ile Arg Thr Lys Ser Asn Thr Ser Arg Lys
            420                 425                 430

Asp Trp Ala Pro Gln Ser Thr Pro Ser Lys Asp Ser Phe His Pro Ser
            435                 440                 445

Ser Leu Met Ser Ala Leu Ile Gln Gln Asp Glu Ser Ile Tyr Leu Cys
450                 455                 460

Pro Pro Ser Ser Pro Ala Leu Leu Asp Ser His Phe Leu Met Gly Ser
465                 470                 475                 480

Val Ser Lys Cys Gly Ser Trp Gln Asp Ser Phe Ala Ala Gly Ser
            485                 490                 495

Glu Ala Ala Leu Lys His Glu Gln Ile Gly His Ala Gln Asp Val Asn
            500                 505                 510

Leu Ala Leu Ser Gly Gly Pro Ser Glu Leu Phe Pro Asp Asn Lys Asn
            515                 520                 525

Asn Asp Leu Tyr Ser Ile Met Arg Asn Leu Gly Ile Asp Phe Glu Asp
            530                 535                 540

Ile Arg Ser Met Gln Asn Glu Glu Phe Phe Arg Thr Asp Ser Thr Ala
545                 550                 555                 560

Ala Gly Glu Val Asp Phe Lys Asp Ile Asp Ile Thr Asp Glu Ile Leu
            565                 570                 575
```

```
Thr Tyr Val Gln Asp Ser Leu Asn Asn Ser Thr Leu Leu Asn Ser Ala
            580                 585                 590

Cys Gln Gln Gln Pro Val Thr Gln His Leu Ser Cys Met Leu Gln Glu
        595                 600                 605

Arg Leu Gln Leu Glu Gln Gln Gln Leu Gln Gln Pro Pro Gln
    610                 615                 620

Ala Leu Glu Pro Gln Gln Leu Cys Gln Met Val Cys Pro Gln
625                 630                 635                 640

Asp Leu Gly Pro Lys His Thr Gln Ile Asn Gly Thr Phe Ala Ser Trp
                645                 650                 655

Asn Pro Thr Pro Pro Val Ser Phe Asn Cys Pro Gln Glu Leu Lys
            660                 665                 670

His Tyr Gln Leu Phe Ser Ser Leu Gln Gly Thr Ala Gln Glu Phe Pro
            675                 680                 685

Tyr Lys Pro Glu Val Asp Ser Val Pro Tyr Thr Gln Asn Phe Ala Pro
    690                 695                 700

Cys Asn Gln Pro Leu Leu Pro Glu His Ser Lys Ser Val Gln Leu Asp
705                 710                 715                 720

Phe Pro Gly Arg Asp Phe Glu Pro Ser Leu His Pro Thr Thr Ser Asn
                725                 730                 735

Leu Asp Phe Val Ser Cys Leu Gln Val Pro Glu Asn Gln Ser His Gly
            740                 745                 750

Ile Asn Ser Gln Ser Ala Met Val Ser Pro Gln Ala Tyr Tyr Ala Gly
            755                 760                 765

Ala Met Ser Met Tyr Gln Cys Gln Pro Gly Pro Gln Arg Thr Pro Val
            770                 775                 780

Asp Gln Thr Gln Tyr Ser Ser Glu Ile Pro Gly Ser Gln Ala Phe Leu
785                 790                 795                 800

Ser Lys Val Gln Ser
                805

<210> SEQ ID NO 3
<211> LENGTH: 2025
<212> TYPE: DNA
<213> ORGANISM: Mus musculus
<220> FEATURE:
<221> NAME/KEY: CDS
<222> LOCATION: (1)..(2022)

<400> SEQUENCE: 3 atg agc agc ggc gcc aac atc acc tat gcc agc cgc aag cgg cgc aag     48
Met Ser Ser Gly Ala Asn Ile Thr Tyr Ala Ser Arg Lys Arg Arg Lys
  1               5                  10                  15 ccg gtg cag aaa aca gta aag ccc atc ccc gct gaa gga att aag tca     96
Pro Val Gln Lys Thr Val Lys Pro Ile Pro Ala Glu Gly Ile Lys Ser
             20                  25                  30 aat cct tct aag cga cac aga gac cgg ctg aac aca gag tta gac cgc    144
Asn Pro Ser Lys Arg His Arg Asp Arg Leu Asn Thr Glu Leu Asp Arg
         35                  40                  45 ctg gcc agc ctg ctg ccc ttc ccg caa gat gtt att aat aag ctg gac    192
Leu Ala Ser Leu Leu Pro Phe Pro Gln Asp Val Ile Asn Lys Leu Asp
     50                  55                  60 aaa ctc tct gtt ctt agg ctc agc gtc acg tac ctg agg gcc aag agc    240
Lys Leu Ser Val Leu Arg Leu Ser Val Thr Tyr Leu Arg Ala Lys Ser
 65                  70                  75                  80 ttc ttt gat gtt gca tta aag tcc acc cct gct gac aga aat gga ggc    288
Phe Phe Asp Val Ala Leu Lys Ser Thr Pro Ala Asp Arg Asn Gly Gly
                 85                  90                  95
```

```
cag gac cag tgt aga gca caa atc aga gac tgg cag gat ttg caa gaa      336
Gln Asp Gln Cys Arg Ala Gln Ile Arg Asp Trp Gln Asp Leu Gln Glu
            100                 105                 110 gga gag ttc ttg tta cag gcg ctg aat ggc ttt gtg ctg gtt gtc aca      384
Gly Glu Phe Leu Leu Gln Ala Leu Asn Gly Phe Val Leu Val Val Thr
        115                 120                 125 gca gat gcc ttg gtc ttc tat gct tcc tcc act atc caa gat tac ctg      432
Ala Asp Ala Leu Val Phe Tyr Ala Ser Ser Thr Ile Gln Asp Tyr Leu
    130                 135                 140 ggc ttt cag cag tct gat gtc atc cat cag agc gta tat gag ctc atc      480
Gly Phe Gln Gln Ser Asp Val Ile His Gln Ser Val Tyr Glu Leu Ile
145                 150                 155                 160 cat aca gaa gac cgg gcg gaa ttc cag cgc cag ctt cac tgg gct cta      528
His Thr Glu Asp Arg Ala Glu Phe Gln Arg Gln Leu His Trp Ala Leu
                165                 170                 175 aac cca gac tct gca caa gga gtg gac gaa gcc cat ggc cct cca cag      576
Asn Pro Asp Ser Ala Gln Gly Val Asp Glu Ala His Gly Pro Pro Gln
            180                 185                 190 gca gca gtc tat tat acc cca gac cag ctt cct cca gag aac gct tct      624
Ala Ala Val Tyr Tyr Thr Pro Asp Gln Leu Pro Pro Glu Asn Ala Ser
        195                 200                 205 ttc atg gag agg tgc ttc agg tgc cgg ctg agg tgc ctg ctg gat aat      672
Phe Met Glu Arg Cys Phe Arg Cys Arg Leu Arg Cys Leu Leu Asp Asn
    210                 215                 220 tca tct ggt ttt ctg gca atg aat ttc caa ggg agg tta aag tat ctt      720
Ser Ser Gly Phe Leu Ala Met Asn Phe Gln Gly Arg Leu Lys Tyr Leu
225                 230                 235                 240 cat gga cag aac aag aaa ggg aag gac gga gcg ctg ctt cct cca caa      768
His Gly Gln Asn Lys Lys Gly Lys Asp Gly Ala Leu Leu Pro Pro Gln
                245                 250                 255 ctg gct ttg ttt gca ata gct act cca ctt cag cca ccc tcc atc ctg      816
Leu Ala Leu Phe Ala Ile Ala Thr Pro Leu Gln Pro Pro Ser Ile Leu
            260                 265                 270 gaa att cga acc aaa aac ttc atc ttc agg acc aaa cac aag cta gct      864
Glu Ile Arg Thr Lys Asn Phe Ile Phe Arg Thr Lys His Lys Leu Ala
        275                 280                 285 cga gga cca ata cgc acc aaa agc aac act agc agg aaa gac tgg gct      912
Arg Gly Pro Ile Arg Thr Lys Ser Asn Thr Ser Arg Lys Asp Trp Ala
    290                 295                 300 ccc cag tca acc cca agt aag gat tct ttc cac ccc agt tct ctt atg      960
Pro Gln Ser Thr Pro Ser Lys Asp Ser Phe His Pro Ser Ser Leu Met
305                 310                 315                 320 agt gcc ctc atc cag cag gat gag tcc atc tat ctg tgt cct cct tca     1008
Ser Ala Leu Ile Gln Gln Asp Glu Ser Ile Tyr Leu Cys Pro Pro Ser
                325                 330                 335 agc cct gcg ctg tta gac agc cat ttt ctc atg ggc tcc gtg agc aag     1056
Ser Pro Ala Leu Leu Asp Ser His Phe Leu Met Gly Ser Val Ser Lys
            340                 345                 350 tgc ggg agt tgg caa gac agc ttt gcg gcc gca gga agt gag gct gcg     1104
Cys Gly Ser Trp Gln Asp Ser Phe Ala Ala Ala Gly Ser Glu Ala Ala
        355                 360                 365 ctg aaa cat gag caa att ggc cat gct cag gac gtg aac ctt gca ctc     1152
Leu Lys His Glu Gln Ile Gly His Ala Gln Asp Val Asn Leu Ala Leu
    370                 375                 380 tct ggc ggc ccc tca gag ctc ttt ccg gat aat aaa aat aat gac ttg     1200
Ser Gly Gly Pro Ser Glu Leu Phe Pro Asp Asn Lys Asn Asn Asp Leu
385                 390                 395                 400 tac agc atc atg agg aac ctt ggg att gat ttt gaa gat atc aga agc     1248
Tyr Ser Ile Met Arg Asn Leu Gly Ile Asp Phe Glu Asp Ile Arg Ser
```

```
                        405                 410                 415
atg cag aac gag gag ttc ttc aga act gac tcc acc gct gct ggt gag        1296
Met Gln Asn Glu Glu Phe Phe Arg Thr Asp Ser Thr Ala Ala Gly Glu
            420                 425                 430 gtt gac ttc aaa gac atc gac ata acg gac gaa atc ctg acc tac gtg        1344
Val Asp Phe Lys Asp Ile Asp Ile Thr Asp Glu Ile Leu Thr Tyr Val
        435                 440                 445 cag gat tcc ctg aac aat tca act ttg ctg aac tcg gct tgc cag cag        1392
Gln Asp Ser Leu Asn Asn Ser Thr Leu Leu Asn Ser Ala Cys Gln Gln
    450                 455                 460 cag cct gtg act cag cac cta agc tgt atg ctg cag gag cgc ctg caa        1440
Gln Pro Val Thr Gln His Leu Ser Cys Met Leu Gln Glu Arg Leu Gln
465                 470                 475                 480 cta gag caa cag caa cag ctt cag cag ccc ccg ccg cag gct ctg gag        1488
Leu Glu Gln Gln Gln Gln Leu Gln Gln Pro Pro Pro Gln Ala Leu Glu
                485                 490                 495 ccc cag cag cag ctg tgt cag atg gtg tgc ccc cag caa gat ctg ggt        1536
Pro Gln Gln Gln Leu Cys Gln Met Val Cys Pro Gln Gln Asp Leu Gly
            500                 505                 510 ccg aag cac acg caa atc aac ggc acg ttt gca agt tgg aac ccc acc        1584
Pro Lys His Thr Gln Ile Asn Gly Thr Phe Ala Ser Trp Asn Pro Thr
        515                 520                 525 cct ccc gtg tct ttc aac tgt ccc cag cag gaa cta aag cac tat cag        1632
Pro Pro Val Ser Phe Asn Cys Pro Gln Gln Glu Leu Lys His Tyr Gln
    530                 535                 540 ctc ttt tcc agc tta cag ggg act gct cag gaa ttt ccc tac aaa cca        1680
Leu Phe Ser Ser Leu Gln Gly Thr Ala Gln Glu Phe Pro Tyr Lys Pro
545                 550                 555                 560 gag gtg gac agt gtg cct tac aca cag aac ttt gct ccc tgt aat cag        1728
Glu Val Asp Ser Val Pro Tyr Thr Gln Asn Phe Ala Pro Cys Asn Gln
                565                 570                 575 cct ctg ctt cca gaa cat tcc aag agt gtg cag ttg gac ttc cct gga        1776
Pro Leu Leu Pro Glu His Ser Lys Ser Val Gln Leu Asp Phe Pro Gly
            580                 585                 590 agg gat ttt gaa ccg tcc ctg cat ccc act act tct aat tta gat ttt        1824
Arg Asp Phe Glu Pro Ser Leu His Pro Thr Thr Ser Asn Leu Asp Phe
        595                 600                 605 gtc agt tgt tta caa gtt cct gaa aac caa agt cat ggg ata aac tca        1872
Val Ser Cys Leu Gln Val Pro Glu Asn Gln Ser His Gly Ile Asn Ser
    610                 615                 620 cag tcc gcc atg gtc agt cct cag gca tac tat gct ggg gcc atg tcc        1920
Gln Ser Ala Met Val Ser Pro Gln Ala Tyr Tyr Ala Gly Ala Met Ser
625                 630                 635                 640 atg tat cag tgc cag cca ggg cca cag cgc acc cct gtg gac cag acg        1968
Met Tyr Gln Cys Gln Pro Gly Pro Gln Arg Thr Pro Val Asp Gln Thr
                645                 650                 655 cag tac agc tct gaa att cca ggt tct cag gca ttc cta agc aag gtg        2016
Gln Tyr Ser Ser Glu Ile Pro Gly Ser Gln Ala Phe Leu Ser Lys Val
            660                 665                 670 cag agt tga                                                            2025
Gln Ser <210> SEQ ID NO 4
<211> LENGTH: 674
<212> TYPE: PRT
<213> ORGANISM: Mus musculus

<400> SEQUENCE: 4

Met Ser Ser Gly Ala Asn Ile Thr Tyr Ala Ser Arg Lys Arg Arg Lys
1               5                   10                  15
```

-continued

Pro Val Gln Lys Thr Val Lys Pro Ile Pro Ala Glu Gly Ile Lys Ser
            20                  25                  30

Asn Pro Ser Lys Arg His Arg Asp Arg Leu Asn Thr Glu Leu Asp Arg
        35                  40                  45

Leu Ala Ser Leu Leu Pro Phe Pro Gln Asp Val Ile Asn Lys Leu Asp
    50                  55                  60

Lys Leu Ser Val Leu Arg Leu Ser Val Thr Tyr Leu Arg Ala Lys Ser
65                  70                  75                  80

Phe Phe Asp Val Ala Leu Lys Ser Thr Pro Ala Asp Arg Asn Gly Gly
                85                  90                  95

Gln Asp Gln Cys Arg Ala Gln Ile Arg Asp Trp Gln Asp Leu Gln Glu
            100                 105                 110

Gly Glu Phe Leu Leu Gln Ala Leu Asn Gly Phe Val Leu Val Val Thr
            115                 120                 125

Ala Asp Ala Leu Val Phe Tyr Ala Ser Ser Thr Ile Gln Asp Tyr Leu
    130                 135                 140

Gly Phe Gln Gln Ser Asp Val Ile His Gln Ser Val Tyr Glu Leu Ile
145                 150                 155                 160

His Thr Glu Asp Arg Ala Glu Phe Gln Arg Gln Leu His Trp Ala Leu
                165                 170                 175

Asn Pro Asp Ser Ala Gln Gly Val Asp Glu Ala His Gly Pro Pro Gln
            180                 185                 190

Ala Ala Val Tyr Tyr Thr Pro Asp Gln Leu Pro Pro Glu Asn Ala Ser
            195                 200                 205

Phe Met Glu Arg Cys Phe Arg Cys Arg Leu Arg Cys Leu Leu Asp Asn
    210                 215                 220

Ser Ser Gly Phe Leu Ala Met Asn Phe Gln Gly Arg Leu Lys Tyr Leu
225                 230                 235                 240

His Gly Gln Asn Lys Lys Gly Lys Asp Gly Ala Leu Leu Pro Pro Gln
                245                 250                 255

Leu Ala Leu Phe Ala Ile Ala Thr Pro Leu Gln Pro Pro Ser Ile Leu
            260                 265                 270

Glu Ile Arg Thr Lys Asn Phe Ile Phe Arg Thr Lys His Lys Leu Ala
            275                 280                 285

Arg Gly Pro Ile Arg Thr Lys Ser Asn Thr Ser Arg Lys Asp Trp Ala
    290                 295                 300

Pro Gln Ser Thr Pro Ser Lys Asp Ser Phe His Pro Ser Ser Leu Met
305                 310                 315                 320

Ser Ala Leu Ile Gln Gln Asp Glu Ser Ile Tyr Leu Cys Pro Pro Ser
                325                 330                 335

Ser Pro Ala Leu Leu Asp Ser His Phe Leu Met Gly Ser Val Ser Lys
            340                 345                 350

Cys Gly Ser Trp Gln Asp Ser Phe Ala Ala Gly Ser Glu Ala Ala
            355                 360                 365

Leu Lys His Glu Gln Ile Gly His Ala Gln Asp Val Asn Leu Ala Leu
    370                 375                 380

Ser Gly Gly Pro Ser Glu Leu Phe Pro Asp Asn Lys Asn Asn Asp Leu
385                 390                 395                 400

Tyr Ser Ile Met Arg Asn Leu Gly Ile Asp Phe Glu Asp Ile Arg Ser
                405                 410                 415

Met Gln Asn Glu Glu Phe Phe Arg Thr Asp Ser Thr Ala Ala Gly Glu
            420                 425                 430

-continued

```
Val Asp Phe Lys Asp Ile Asp Ile Thr Asp Glu Ile Leu Thr Tyr Val
        435             440             445
Gln Asp Ser Leu Asn Asn Ser Thr Leu Leu Asn Ser Ala Cys Gln Gln
        450             455             460
Gln Pro Val Thr Gln His Leu Ser Cys Met Leu Gln Glu Arg Leu Gln
465             470             475             480
Leu Glu Gln Gln Gln Gln Leu Gln Gln Pro Pro Gln Ala Leu Glu
            485             490             495
Pro Gln Gln Gln Leu Cys Gln Met Val Cys Pro Gln Gln Asp Leu Gly
            500             505             510
Pro Lys His Thr Gln Ile Asn Gly Thr Phe Ala Ser Trp Asn Pro Thr
        515             520             525
Pro Pro Val Ser Phe Asn Cys Pro Gln Gln Glu Leu Lys His Tyr Gln
        530             535             540
Leu Phe Ser Ser Leu Gln Gly Thr Ala Gln Glu Phe Pro Tyr Lys Pro
545             550             555             560
Glu Val Asp Ser Val Pro Tyr Thr Gln Asn Phe Ala Pro Cys Asn Gln
            565             570             575
Pro Leu Leu Pro Glu His Ser Lys Ser Val Gln Leu Asp Phe Pro Gly
            580             585             590
Arg Asp Phe Glu Pro Ser Leu His Pro Thr Thr Ser Asn Leu Asp Phe
        595             600             605
Val Ser Cys Leu Gln Val Pro Glu Asn Gln Ser His Gly Ile Asn Ser
        610             615             620
Gln Ser Ala Met Val Ser Pro Gln Ala Tyr Tyr Ala Gly Ala Met Ser
625             630             635             640
Met Tyr Gln Cys Gln Pro Gly Pro Gln Arg Thr Pro Val Asp Gln Thr
            645             650             655
Gln Tyr Ser Ser Glu Ile Pro Gly Ser Gln Ala Phe Leu Ser Lys Val
            660             665             670
Gln Ser
```

TRANSGENIC MOUSE EXPRESSING CONSTITUTIVELY ACTIVE HYDROCARBON RECEPTOR

The present invention relates to a mutant construct for a constitutively active aryl hydrocarbon receptor (CA-AhR), a transgenic non-human animal expressing CA-AhR, and an animal model for the study of the molecular mechanisms of cancer, in particular stomach cancer. The invention also relates to methods of screening and/or investigating carcinogenic and anti-carcinogenic compounds, screening and/or investigating drug candidates, as well as compounds discovered or developed using this method.

BACKGROUND OF THE INVENTION

The dioxin/aryl hydrocarbon receptor (AhR) belongs to a specific class of transcription factors, basic helix-loop-helix/Per-Arnt-Sim domain (bHLH/PAS) proteins, which is emerging as an important battery of regulatory factors seemingly designed to respond to environmental cues. Other members of this family include the hypoxia-inducible factor HIF-1α, the rhythmicity regulatory protein Clock, the neuro-regulatory protein Sim, and Arnt, an essential partner factor for all of the factors mentioned above including the AhR (1). Arnt is recruited to the AhR in a ligand-dependent manner to facilitate recognition of xenobiotic response elements of target promoters.

The ligand-activated AhR mediates transcriptional activation of a network of genes encoding enzymes such as CYP1A1, CYP1A2, glutathione S-transferase Ya, UDP-glucuronosyl-transferase 1A6 and NAD(P)H quinone oxidoreductase-1 that function in the oxidative metabolism of xenobiotics (2). Well-characterized ligands of the AhR are polycyclic aromatic hydrocarbons formed during combustion processes and polychlorinated dioxins and, coplanar biphenyls that contaminate industrial chemicals and the environment (2). Thus, AhR-mediated signalling pathways provide a first line of defence against potentially toxic environmental pollutants. On the other hand, induction of oxidative metabolic processes by the AhR can also cause the production of highly carcinogenic metabolites, creating a strong link between AhR activation and chemical carcinogenesis (3). In addition, the receptor appears to mediate by as yet unclear mechanisms a wide range of toxic effects by chlorinated dioxins including birth defects, impaired reproductive capacity, and immune suppression (1). A number of independent loss-of-function studies performed by gene disruption in mice have not yielded conclusive information with regard to a possible developmental role of the receptor (4–7). In view of its critical role in mediating metabolic responses to environmental pollutants, the sole biological function of the AhR could therefore be restricted to regulation of adaptive responses to xenobiotics. This notion seems to be corroborated by the fact that a putative physiological function of the AhR remains to be determined. Against this background the present inventors have performed a gain-of-function study to examine possible biological functions of the AhR system. To this end, a constitutively active AhR mutant (CA-AhR) was created and expressed in transgenic nice to study possible AhR-mediated biological effects that are generated in the absence of any exposure to environmental contaminants.

PRIOR ART

U.S. Pat. No. 5,378,822 discloses recombinant DNA molecules which encode murine and human Ah receptors, which are used to generate large quantities of Ah-receptor protein for use in competitive binding assays used for detecting environmental pollutants or for regulating gene expression in response to receptor agonists. Another use is for the generation of recombinant organisms that can serve as biomonitors for environmental pollutants, or for detecting human and wildlife populations that have high susceptibility to environmental pollutants.

SUMMARY OF THE INVENTION

The present invention makes available a powerful tool for the study of cancer, based on a novel expression construct for a constitutively active hydrocarbon receptor CA-AhR. The invention further comprises transgenic non-human animals, preferably mammals, expressing CA-AhR in one or more tissues thereof. An animal model based on said transgenic non-human animals forms the basis for novel methods e.g. for the study of cancer; for the screening of compounds, such as drug candidates; for the investigation of the molecular mechanisms of cancer, in particular stomach cancer; for the investigation of the mechanisms of highly differentiated adenocarcinoma etc. Likewise, an in vitro model based on transformed cells or cell lines, functionally incorporating the inventive construct are disclosed.

The invention will be further defined in the description, examples and attached claims, hereby incorporated in their entirety.

BRIEF DESCRIPTION OF THE DRAWINGS

The invention will be described in closer detail in the description and examples below, with reference to the attached drawings, in which.

DESCRIPTION

Figure 1:
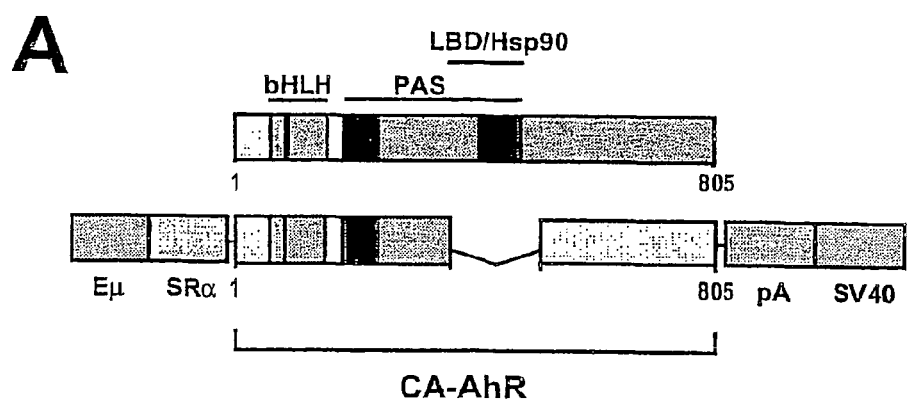
FIG. 1 shows the constitutive activity of CA-AhR. (A) Schematic representation of the wild type mouse AhR (mAhR) and of CA-AhR. (B) Functional activity of CA-AhR in CHO cells. Cells were transiently transfected with an AhR-dependent luciferase reporter gene, and expression vectors encoding Arnt, wild type AhR, or CA-AhR. The control lanes (Ctrl) represent activity from the reporter gene alone and empty expression plasmid. Data are from one experiment performed in duplicate and are representative of at least three independent experiments. (C) Detection of the AhR and CA-AhR proteins expressed following transient transfection of CHO cells. Whole cell extracts were analyzed by immunoblotting using anti-AhR antibodies. The star indicates non-specific immuno-reactivity. (D) Expression and functional activity of CA-AhR in 8 month old female mice. RNA blot analysis (2 μg poly-A RNA) showing expression of the endogenous AhR, CA-AhR and the target genes CYP1A1 and CYP1A2. The expression of glyceraldehyde-3-phosphate dehydrogenase (GAPDH) is shown as RNA loading control of corresponding tissues.
Figure 1:
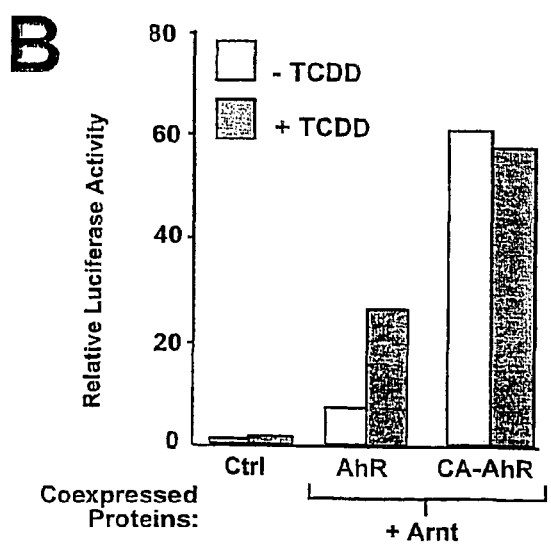
Figure 1:
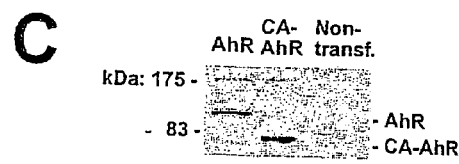
Figure 1:
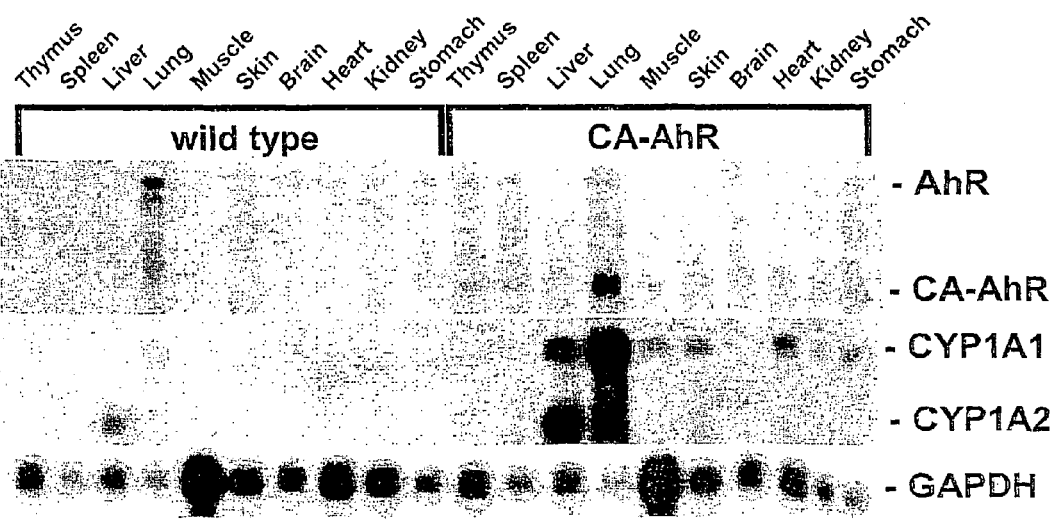

Before the present construct, transgenic animals incorporating said construct, animal models and methods, based on the use of said animals, are disclosed and described, it is to be understood that this invention is not limited to the particular configurations, process steps, and materials disclosed herein as such configurations, process steps, and materials may vary somewhat. It is to be understood that the terminology employed herein is used for the purpose of describing particular embodiments only and is not intended to be limiting since the scope of the present invention will be limited only by the appended claims and equivalents thereof.

In the description, examples, and claims, the following abbreviations will be used: AhR=Aryl hydrocarbon (dioxin) receptor; Arnt=AR nuclear translocator; CA-AhR=Constitutively Active AhR; CYP1A1=Cytochrome P450 1A1; HE=Hematoxylin-Eosin; TCDD=2,3,7,8-tetrachlorodibenzo-p-dioxin.

The present inventors have surprisingly found that expression of CA-AhR in transgenic mice induces a pronounced lethality beginning at six months of age, correlating with the development of severe tumours in the stomach. Thus, this study clearly demonstrates the oncogenic potential of the AhR. It has been difficult to unambiguously interpret the histopathology of the stomach tumours in the CA-AhR mice. The well-organised glandular structures and the low levels of cellular atypia argue for a benign phenotype. On the other hand, the reduced life span, the aggressive, expanding invasion of all stomach layers and the adherence to surrounding organs point toward a more malignant phenotype. Intestinal metaplasia was widespread in the CA-AhR tumours and this is regarded as a pre-cancerous lesion (17). Furthermore, a subgroup of human intestinal-type gastric carcinoma has recently been described where the cancer cells also are highly differentiated (18). Given the striking gastric oncogenic phenotype of the CA-AhR mice it is interesting to note that the most physiological candidates of receptor ligands are indole derivatives, most notably indolo [3,2-b]carbazole that are generated in the acidic environment of the stomach from dietary precursors, e.g. indolo-3-carbinol (19). Moreover, certain food-born heterocyclic amines that are generated during the food cooking process also constitute AhR ligands (20). Thus, the correlation between presence of putative dietary receptor ligands and a possible role of the AhR in homeostatic control of cells of the gastric mucosa presents an intriguing biological scenario that remains to be scrutinised in closer molecular detail.

Stomach cancer is the second most common human malignancy in the world (21). The role (if any) of the AhR in development of this cancer form is not known. Interestingly, stomach cancer is more commonly found in men than in women (21, 22), a sex difference that is reflected in the CA-AhR mice. Some epidemiological studies show an increased incidence of stomach cancer in human populations exposed to herbicides (23) or fatty fish (24) contaminated with TCDD or other dioxins. More commonly discussed risk factors for stomach cancer is diet containing mutagenic nitrosating compounds, as well as infection with *Helicobacter pylori* (22). However, the CA-AhR animals in this study received conventional rodent feed, and no infection by Helicobacter was detected by selective culture of tissue homogenates (data not shown). Given the absence of any known carcinogen, it is unlikely that induction of drug metabolising enzymes and ensuing bioactivation of mutagens can explain the oncogenic effect of the AhR. A more intriguing hypothesis is that a network of critical growth control genes is dysregulated by the CA-AhR.

In the stomach mucosa high levels of endogenous AhR mRNA are detected on gestational day 15.5 of the developing mouse (25). The present inventors have detected expression of the CA-AhR in the stomach of new-born mice (data not shown). Thus, it is very probable that the present mouse model reflects a situation of early in utero exposure to AhR ligands, which continues post-natally. Strikingly, there is a paucity of data with regard to the long-term effects following in utero exposure to dioxins and other environmental pollutants constituting AhR ligands. In addition to dioxins xenobiotic AhR ligands include halogenated biphenyls, and a large number of non-halogenated polycyclic aromatic hydrocarbons, e.g. benzo[a]pyrene, 9,10-dimethylbenz[a] anthracene, and 3-methylcholanthrene. In this context it is noteworthy that the AhR has recently been proposed to differentially regulate various target genes depending on the chemical nature of the receptor ligand (26). The AhR has been reported to activate Bax gene transcription when exposed to 9,10-dimethylbenz[a]anthracene but not when occupied with TCDD as ligand (26). Obviously, this model needs to be further substantiated. Strikingly, the present model system may provide an experimental tool to resolve this issue. Notably, the possible biological effects mediated by the activated receptor per se (i.e. produced by the CA-AhR) can be compared to the effects produced by the various ligand-stimulated receptor forms. However, this scenario needs to be further experimentally elucidated, taking into account that all classes of receptor ligands may not yet have been identified.

Interestingly, several species of laboratory animals treated with AhR ligands have been reported to develop lesions in the glandular stomach mucosa that resemble the findings in the CA-AhR mice of the present invention. For instance, adenocarcinoma is observed after injection of 3-methylcholantrene into the stomach wall of several strains of mice (27, 28). Whether caused by reactive 3-methylcholantrene metabolites or some other mechanism, a potential role for the AhR in 3-methylcholantrene-induced stomach cancer is supported by the observation that the DBA mouse strain expressing a low affinity variant is resistant to developing 3-methylcholantrene-induced stomach tumours (27). In addition, hyperplasia of the gastric mucosa and cysts in the submucosa of Rhesus monkeys (29) and adenocarcinoma of rat glandular stomach (30) have been observed after exposure to dietary mixtures of polychlorinated biphenyls that have the potential to activate the AhR. Taken together, these observations indicate an important role of the AhR in gastric tumorigenesis and thus also in the control of growth and proliferation of gastric epithelial cells.

There exist seemingly contradictory reports on the role of the AhR in cell cycle control. TCDD has been reported to stimulate growth of human keratinocytes (31), and mutant cells that express no or substantially reduced levels of AhR display decreased growth rates in comparison to wild type cells (32, 33). On the other hand, TCDD has been reported to induce expression of the cyclin/cdk inhibitor p27 (Kip1) in certain cells (34). Interestingly, mice develop adenocarcinomas in the glandular stomach upon expression of viral oncoproteins binding the retinoblastoma protein Rb (35–38). Notably, the AhR has recently been reported to physically interact with Rb (39, 40) via an as yet unclear mechanism, and it remains to be established whether this effect is of any relevance for the phenotype of the CA-AhR expressing mice.

Interestingly, mice overexpressing TGFα or EGF-like viral growth factors show cystic hyperplasia, intestinal metaplasia and dysplasia in the stomach (41, 42). Moreover, TGFα mRNA expression levels are known to be induced by TCDD treatment of e.g. keratinocytes (43). However, the present inventors failed to detect any increase in TGFα mRNA levels in the glandular stomach of the CA-AhR mice (data not shown). Thus, it will now be important to identify the network of genes that is dysregulated upon expression of the CA-AhR and to thereby understand a possible physiological role of the AhR in gastric homeostasis.

In conclusion, the present inventors have demonstrated that CA-AhR induces development of highly invasive stomach tumours in the absence of exposure to any known carcinogen. This study provides for the first time evidence of the direct oncogenic potential of the AhR and suggests a possible physiological role of the AhR in homeostatic control of cells of the gastric mucosa.

Consequently, the present invention makes available an expression construct for a constitutively active hydrocarbon receptor (CA-AhR), and in particular a mutant construct.

According to one embodiment of the invention, the construct is lacking a portion of the ligand binding domain. According to a particular embodiment, presently preferred by the inventors, said construct comprises a mouse AhR sequence lacking amino acids 288–421.

The invention further makes available a transgenic non-human animal expressing CA-AhR in one or more tissues thereof or a transgenic non-human animal functionally incorporating an expression construct as defined above.

The transgenic non-human animal according to the invention is preferably selected from the group consisting of mice, rats, moneys, sheep and rabbits.

The present invention also encompasses an isolated cell of the inventive transgenic nonhuman animal as defined above. The invention also encompasses an isolated cell line derived from the transgenic animal as defined above. According to one embodiment, the cell or cells is/are selected from a germ cell or a somatic cell.

The present invention makes available an animal model for the study of cancer, comprising a transgenic non-human animal comprising an expression construct for a constitutively active hydrocarbon receptor (CA-AhR) in at least one of its cells. The transgenic animal according to the invention is preferably selected from the group consisting of mice, rats, moneys, sheep and rabbits.

The present invention also makes available an in vitro model for the study of cancer, comprising a cell having comprising an expression construct for a constitutively active hydrocarbon receptor (CA-AhR) functionally incorporated. The invention further makes available an in vitro model for the study of cancer, comprising a cell line, the cells of which comprising an expression construct for a constitutively active hydrocarbon receptor (CA-AhR) functionally incorporated.

An important embodiment of the present invention is a method for the screening of drug candidates, wherein the anti-carcinogenic effect of said drug candidates is assessed in a non-human transgenic animal or a cell or cell line thereof expressing a constitutively active hydrocarbon receptor (CA-AhR).

Another embodiment is a method for the screening of drug candidates, wherein the anti-carcinogenic effect of said drug candidates is assessed in an animal model, or in an in vitro model as defined above.

Another embodiment is a method for investigating the molecular mechanisms of cancer, wherein an animal model or in vitro model as defined above is used.

The invention also makes available a method for investigating the mechanisms of highly differentiated adenocarcinoma in the stomach, wherein an animal model or in vitro model as defined above is used.

The invention further makes available a method of inducing stomach cancer in a non-human animal for research purposes, wherein said animal is transformed with a construct expressing a constitutively active hydrocarbon receptor (CA-AhR). Transformed with the construct in this context means that the construct is functionally inserted, i.e. in proper reading frame and orientation, as is well understood by persons skilled in the art. Different expression vectors or systems are well known.

According to one embodiment of the present invention, the construct is injected into a fertilised egg of said nonhuman animal and the egg permitted to develop into an animal containing said construct in its genome.

Further, the invention makes available a method of inducing drug metabolising enzymes normally regulated by the Ah-receptor in the presence of a ligand for the study of drug metabolism by any member (-s) of said enzymes, wherein a non-human animal is transfected with a construct expressing a constitutively active hydrocarbon receptor (CA-AhR).

According to one embodiment of the above method, an in vitro method of inducing drug metabolising enzymes normally regulated by the Ah-receptor in the presence of a ligand for the study of drug metabolism by any member (-s) of said enzymes is assembled by transfecting cultured cells with a construct expressing a constitutively active hydrocarbon receptor (CA-AhR).

The present invention, by making the above practical and powerful research and screening tools available, also encompasses drug candidates, prodrugs and treatment regimens identified by a process involving a method, an animal method or an in vitro method involving animals or cells functionally incorporating a construct expressing a constitutively active hydrocarbon receptor (CA-AhR).

In the context of drug-developments and the understanding of the molecular mechanisms of cancer, other animals than mice are also of interest, especially other mammals. Rodents, for example, are widely used and especially rats and mice. As the inventive construct also can be transformed into and the CA-Ah receptor expressed in other animals, the present invention also encompasses the use of the construct in such other animals, animal models and methods based thereon.

EXAMPLES

Materials and Methods

Cell Culture, Reporter Gene and Immunoblot Assays: CHO cells were transiently transfected with an XRE-containing luciferase reporter gene construct, PTXDIR, and CMV expression plasmids encoding Arnt and either the wild type mouse AhR (8) or a mouse AhR lacking a portion of the ligand binding domain (amino acids 288–421), CA-AhR (J. McGuire, K. Okamoto, M. L. Whitelaw, H. Tanaka, L. Poellinger, studies performed, manuscript in preparation). After 48 h of incubation either in the presence of 10 nM TCDD (2,3,7,8-tetrachlorodibenzo-p-dioxin) or vehicle (1% DMSO) alone, luciferase activity was assayed. Whole cell extracts were prepared as previously described (8) to monitor expression of the AhR. The extracts (30 μg protein) were separated by 7.5% SDS-PAGE, transferred to nitro-cellulose membrane and relative expression levels determined by immunodetection with anti-AhR antiserum (BioMol, PA).

Mice: The CA-AhR was subcloned between the mouse IgH intron enhancer/SV40 promoter and the SV40 polyadenylation site of pEμSR (9). Transgenic mice were created by pronuclear injection of a 5.5 kb KpnI fragment encompassing the EμSR-CA-AhR construct into fertilised C57BL/6×CBA eggs, resulting in five founder animals carrying the CA-AhR construct in the genome. Three lines were chosen for further studies and subsequently crossed into the C57BL/6 strain for two additional generations. Transgenic CA-AhR and wild type control animals were of the same mixed genetic background. Homozygosity was verified by Southern blot analysis of genomic DNA from tail biopsies. Animals were held in ventilated filter-top cages and received conventional rodent feed (RM3, Special Diet Services) and tap water ad libitum, and were exposed to a 12-hour light/dark cycle. In TCDD exposure studies, age-matched wild type and CA-AhR female mice were treated with corn oil or various doses of TCDD dissolved in corn oil and were sacrificed three days later. Animals were sacrificed by $CO_2$ asphyxiation followed by cervical dislocation. All animal procedures were approved by the local ethical committee.

The sex ratio of all CA-AhR animals was 216 males and 209 females, and of the homozygous CA-AhR mice 125 males and 107 females, compared to 245 males and 246 females of the wild type mice.

Wild type and homozygous CA-AhR animals were weighed once a week during the first 3 months of life. Even though individual litters differed in weight gain, no difference was observed in either sex when average weights of 5 litters of each genotype were compared (45 wild type and 44 CA-AhR animals in total).

RNA Isolation and Northern Blot Assay: Total RNA was prepared by tissue homogenisation in a guanidinium thiocyanate buffer followed by $CsCl_2$-gradient centrifugation (10). Poly-A RNA was isolated from total RNA using oligo-(dT)-coupled magnetic beads (Dynal AS, Oslo, Norway). Northern blot analysis was carried out according to standard methods (10). Prehybridization and hybridization was carried out at 42° C. in a formamide-containing buffer (10). The filters were hybridised overnight with $^{32}$P-labelled cDNA probes specific for the genes indicated (11). The filters were washed with 2×SSPE at room temperature, 30 minutes 2×SSPE/2% SDS at 65° C. and 30 minutes 0.1×SSPE/0.1% SDS at 65° C. and subsequently exposed to autoradiographic film at −70° C. and PhosphorImager analysis (FujiFilm Inc.). The PhosphorImager results were quantified using the software provided by the manufacturer.

Histopatholopical Analysis: Tissues were removed and fixed in 4% buffered formaldehyde, embedded in paraffin and cut into 4 μm thick sections that were stained with Hematoxylin-Eosin, Alcian Blue pH 2.5 or van Gieson stain according to standard procedures.

Results

In analogy to nuclear hormone receptors (12), the ligand binding domain of the AhR mediates both activation of receptor function in the presence of ligand and repression of receptor function in the absence of ligand (8, 13). Partial deletion of the minimal ligand-binding domain of the AhR results in a protein, CA-AhR (FIG. 1A), that fails to bind ligand (data not shown). This truncated receptor was constitutively active with regard to reporter gene activation (FIG. 1B) in transient transfection experiments, at CA-AhR expression levels matching those of the ligand-dependent wild type AhR (FIG. 1C).

CA-AhR was expressed in transgenic mice under the control of an SV40 promoter and the immunoglobulin heavy chain (IgH) intron enhancer (9). Mating heterozygous CA-AhR animals yielded wild type, hetero-, and homozygous mice at a normal Mendelian 1:2:1 frequency, indicating no prenatal lethality of homozygous mutants. Both heterozygous and homozygous CA-AhR mice were fertile and showed a normal sex ratio. In agreement with other studies using IgH intron enhancer-driven expression constructs (9, 14), CA-AhR mRNA expression levels were detected in thymus and spleen (FIG. 1D) and in enriched B and T cells (data not shown) as well as in a number of non-lymphoid tissues (FIG. 1D). The ligand-activated AhR regulates expression of a battery of genes encoding xenobiotic metabolising enzymes, e.g. CP1A1 and CYP1A2 (1). With the exception of the lung, expression of CYP1A1 mRNA was not detected in untreated wild-type mice (FIG. 1D). In contrast, all tissues that showed CA-AhR transgene expression also demonstrated induced expression at various levels of CYP1A1 mRNA (FIG. 1D). However, the variation in induced expression of this target gene did not correlate with the expression levels of CA-AhR, indicating that additional tissue-specific factors are important for the regulation of CYP1A1 expression. In addition, in the liver expression of CYP1A2 mRNA was also induced by the transgene. Taken together, this demonstrates that CA-AhR is transcriptionally active and mimics the action of the ligand-activated AhR.

Figure 2:
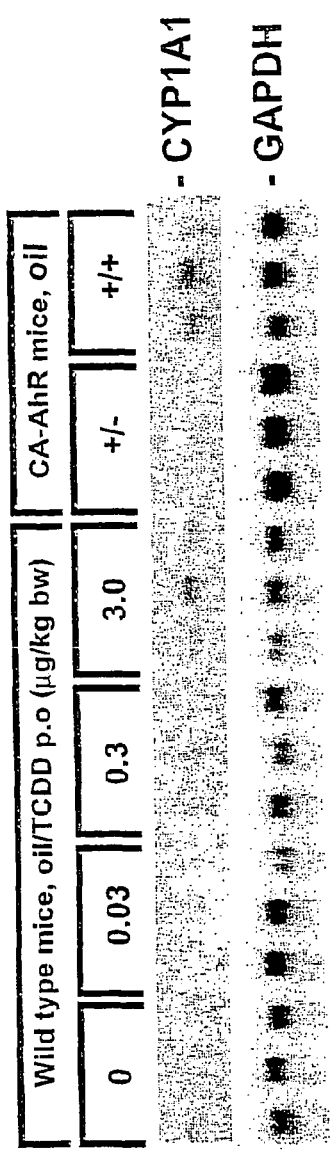
FIG. 2 shows the functional activity of CA-AhR in the mouse thymus and mortality time course. (A) RNA blot (30 μg total RNA) showing expression of CYP1A1 mRNA in thymus of six month old wild type versus age-matched heterozygous and homozygous CA-AhR mice, treated with vehicle (corn oil) or TCDD as indicated. (B) The relative thymus weight (g/g body weight) was decreased in homozygous CA-AhR animals up to six months of age. Closed bars represent wild type and open bars represent CA-AhR animals. At least four female animals of each genotype and age were examined. The star indicates p<0.05, as assessed by two-tailed Students t-test. (C) Ages of the homozygous CA-AhR mice found dead stratified by sex (closed symbols for males, open for females) and strain (triangles for strain "A3" and circles for strain "Y8").
Figure 2:
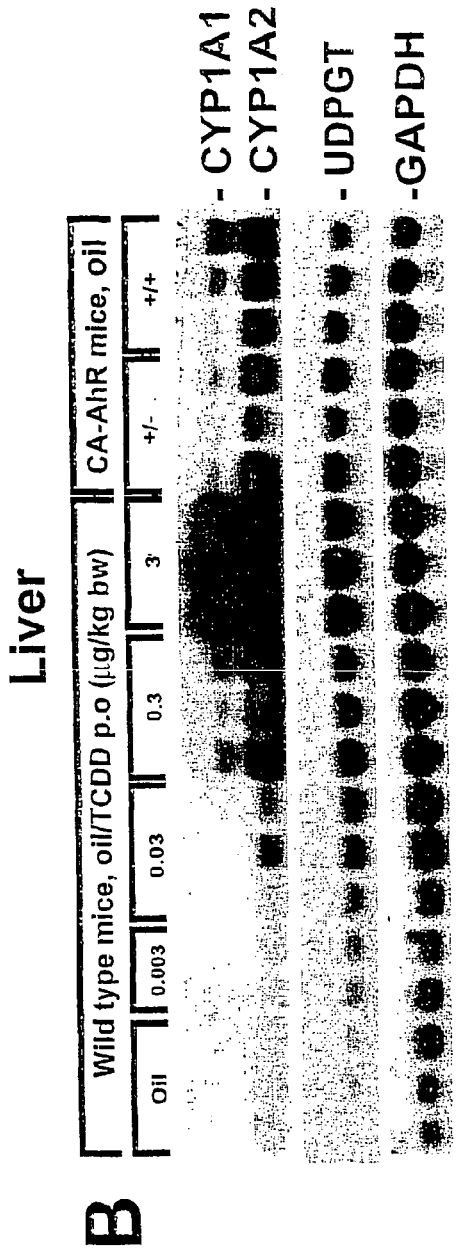
Figure 2:
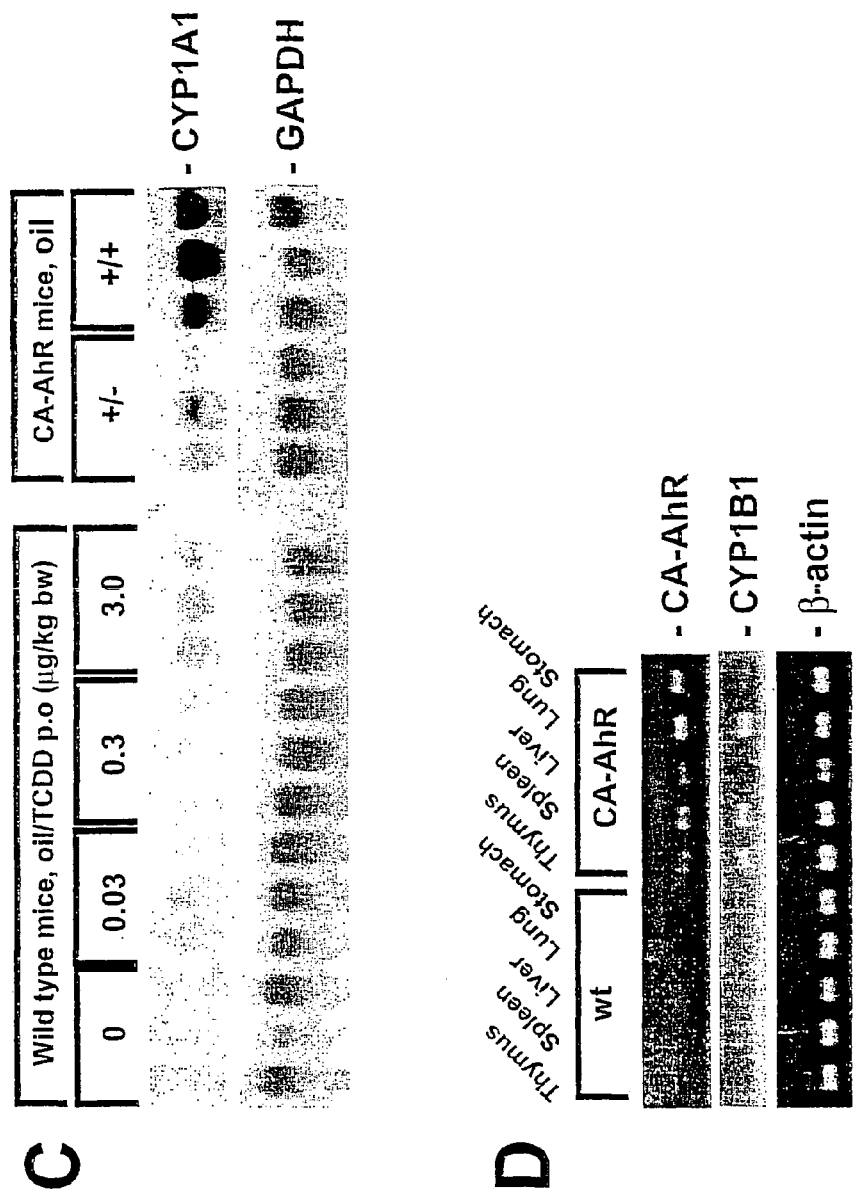

To assess the level of functional activity of CA-AhR, induction of CYP1A1 mRNA expression by CA-AhR in the thymus was compared to the induction response produced in wild-type nice following oral exposure to TCDD. In homozygous CA-AhR mice, the levels of CYP1A1 mRNA were comparable to those observed in wild type mice treated with a single dose of TCDD of3 µg TCDD/kg body weight (FIG. 2A). Upon exposure to this dose of TCDD no acute toxic effects (e.g. lethality or the wasting syndrome) are seen in mouse models (15). No effect on body weight gain was observed in either male or female CA-AhR mice (data not shown). These results are in agreement with the fact that weight loss or impaired weight gain are only detected when mice are exposed to doses of TCDD considerably higher than 3 µg/kg body weight (2, 15). Thus, the activity of the CA-AhR seems to correspond to a chronic, relatively low dose exposure to TCDD or other AhR ligands.

A well-characterized adverse effect of dioxin is involution of the thymus (1). The relative thymus weight of CA-AhR animals was decreased up to six months of age (FIG. 2B). Altered population sizes of single positive $CD8^+$ and $CD4^+$ T cells have previously been observed in rats exposed to TCDD during gestation (16). This effect was also observed in thymi from new-born CA-AhR mice (data not shown). These results indicate that in the absence of dioxin, CA-AhR mimicked biological effects that are normally elicited by the dioxin-activated form of the AhR.

The CA-AhR mice showed a significantly reduced life span where only very few homozygous animals survived past an age of 12 months. Several mice were found dead, beginning already at six months of age, most often without any preceding clinical symptoms. Notably, there was a striking sex difference in that male mice died earlier than females. In addition, a difference in the time-course between two independent homozygous lines of mice was also observed (FIG. 2C).

Figure 3:
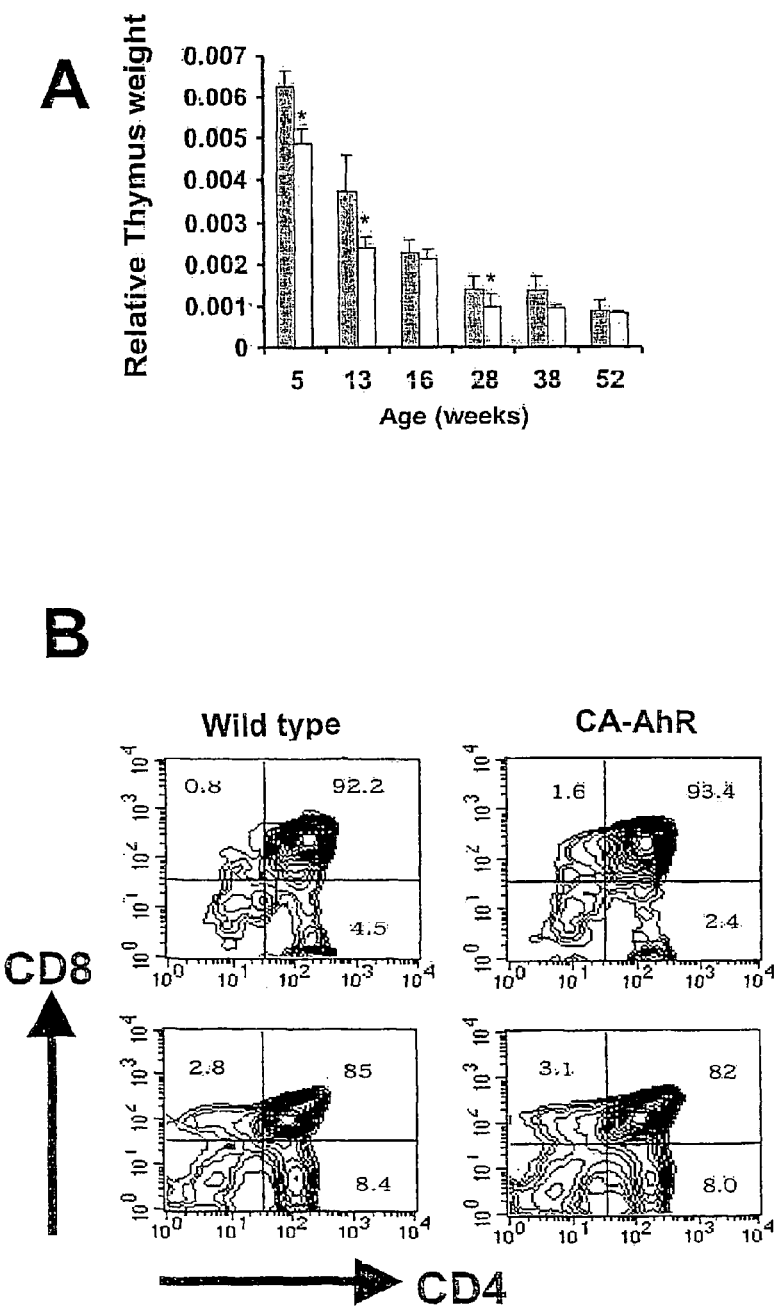
FIG. 3 shows how striking neoplastic lesions are observed in the stomach. (A) Normal stomach from a 12 month old wild type male showing the forestomach (fs) and the glandular stomach (gs). (B) At 3–4 months of age single small cysts close to the limiting ridge were seen in CA-AhR mice (arrow). (C) In older CA-AhR animals (6–12 months) the cystic tumours were more numerous and occupied a larger area of the stomach. (D) In the most severe cases (9–12 months of age), the stomach was adherent to adjacent organs such as spleen (sp), pancreas (panc) and liver (liv). (E) Normal stomach from a 6 month old wild type male mouse showing the muscularis propria layer (mp) and the limiting ridge (lr) constituting the border between the squamous epithelium of the foreststomach (fs) and the glandular epithelium (ge; Hematoxylin and Eosin staining [HE], bar=0.5 mm). (F) Close to the limiting ridge a rupture of the submucosa by neoplastic crypts is seen in a 3.5 month old CA-AhR male. Note glands within the stroma of the limiting ridge (HE, bar=0.5 mm). (G) Larger magnification of boxed area in FIG. 3F (HE, bar=0.15 mm). (H) Stomach from a 12 month old CA-AhR male with severely distorted tissue architecture (HE, bar=1.25 mm). (I) Glands underlying the serosa (ser) in a 12 month old CA-AhR female with characteristics of a hamartoma (ham), i.e. a defined structure containing lymphatic tissue, vessels and fat (HE, bar=0.5 mm). Note also invasion (arrow) of glands from the glandular epithelium (ge) into the muscularis propria (mp).

At necropsy, dramatic stomach lesions were observed in the CA-AhR mice. In contrast to stomachs from wild type mice (FIG. 3A), CA-AhR mice demonstrated grossly visible cysts at 3–4 months of age in the lesser curvature of the stomach (FIG. 3B). The cysts became more numerous with age (FIG. 3C) and in the most severe cases (around 12 months of age), the growths adhered to surrounding organs such as liver, pancreas and abdominal fat (FIG. 3D). In many cases, the stomach wall was thickened throughout the cardia and corpus region of the glandular stomach. The limiting ridge, which defines the border between the forestomach and the glandular part of the rodent stomach (FIG. 3E), was also macroscopically substantially enlarged (data not shown).

Histopathological analysis revealed glandular structures expanding from the mucosa into the stroma of the limiting ridge, explaining the thickening observed at gross inspection (FIG. 3F). The expansive growth of the cystic glandular structures in the mucosa showed invasion of dysplastic crypts into the submucosa, muscularis propria and eventually into the subserosal region (FIGS. 3F, G). In spite of the aggressive behaviour of the invading tumour cells, they retained a remarkably well differentiated appearance after passing through the muscularis mucosa (FIG. 3G). The tumour development progressed over time resulting in a bizarre, distorted tissue architecture observed prior to lethality (12 months of age, FIG. 3H).

Figure 4:
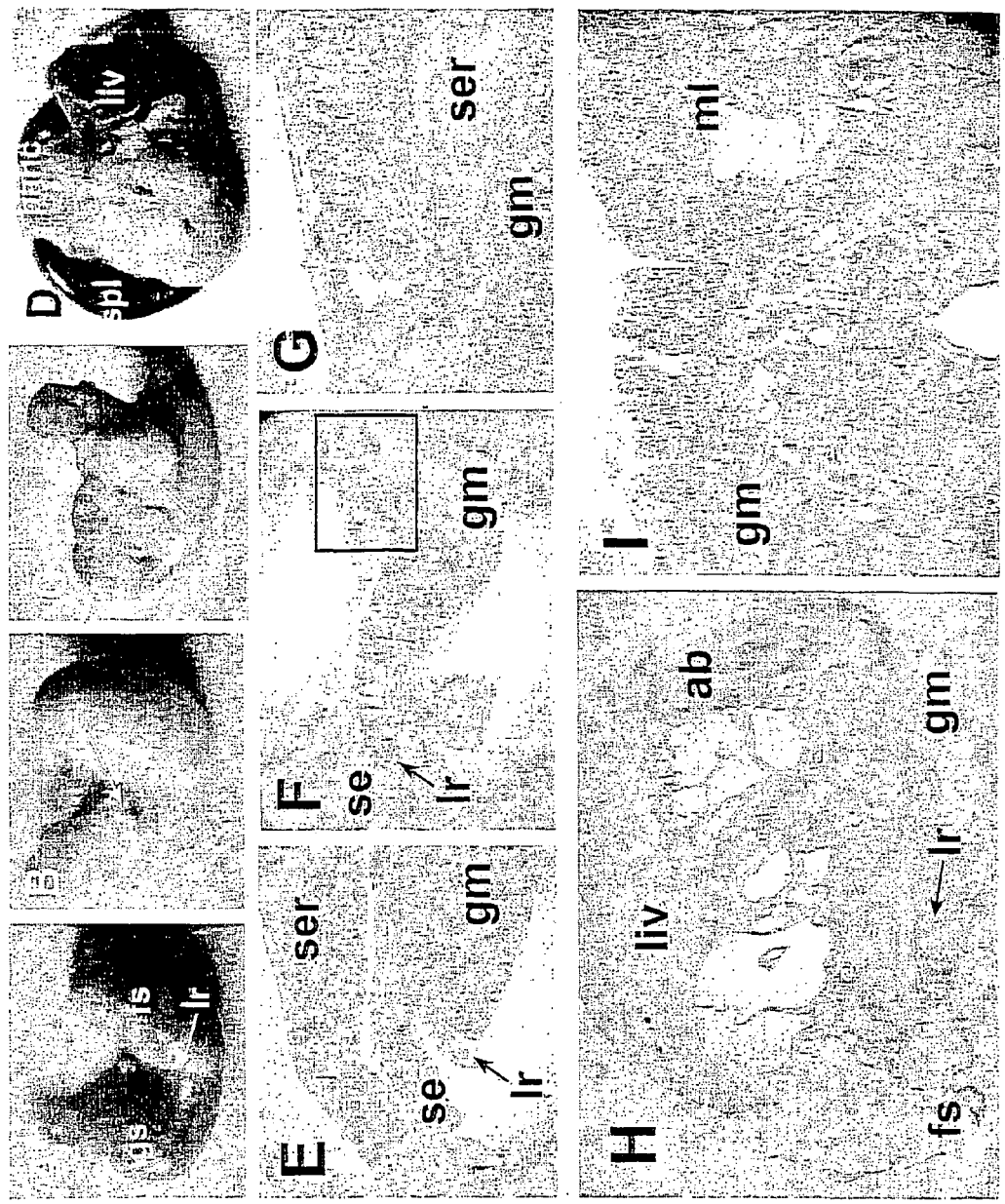
FIG. 4 shows intestinal metaplasia, adherence to adjacent organs and expression of CA-AhR in the gastrointestinal tract. (A, B) Glandular structures located in the muscularis propria with cells resembling foveolar epithelium (fe) and pyloric glands (pg) showing intestinal metaplasia in a 9 month old CA-AhR male. Stainings: Hematoxylin and Eosin (HE; panel A) and Alcian Blue pH 2.5 (panel B). Bars=0.1 mm. (C, D) Invading crypts surrounded by connective tissue (ct) invade the submucosa (sm) by penetrating through the muscularis mucosa (mm), submucosa (sm) layers and into the muscularis propria (mp) in a 9 month old CA-AhR female. Stainings: HE (panel C) and van Gieson (panel D). Bars=0.1 mm. (E, F) Squamous cysts on the caecum showing colonic glands (cg) and squamous epithelium (sq.e) of a 9 month old CA-AhR male (HE, bar=0.5 mm). (G) The expression and activity of CA-AhR in the alimentary tract is highest in the glandular stomach. RNA blot (2 μg poly-A RNA) showing expression of CA-AhR, endogenous AhR (AhR), CYP1A1 and GAPDH mRNA in different parts of the alimentary tract of homozygous CA-AhR mice three months of age.
Figure 4:
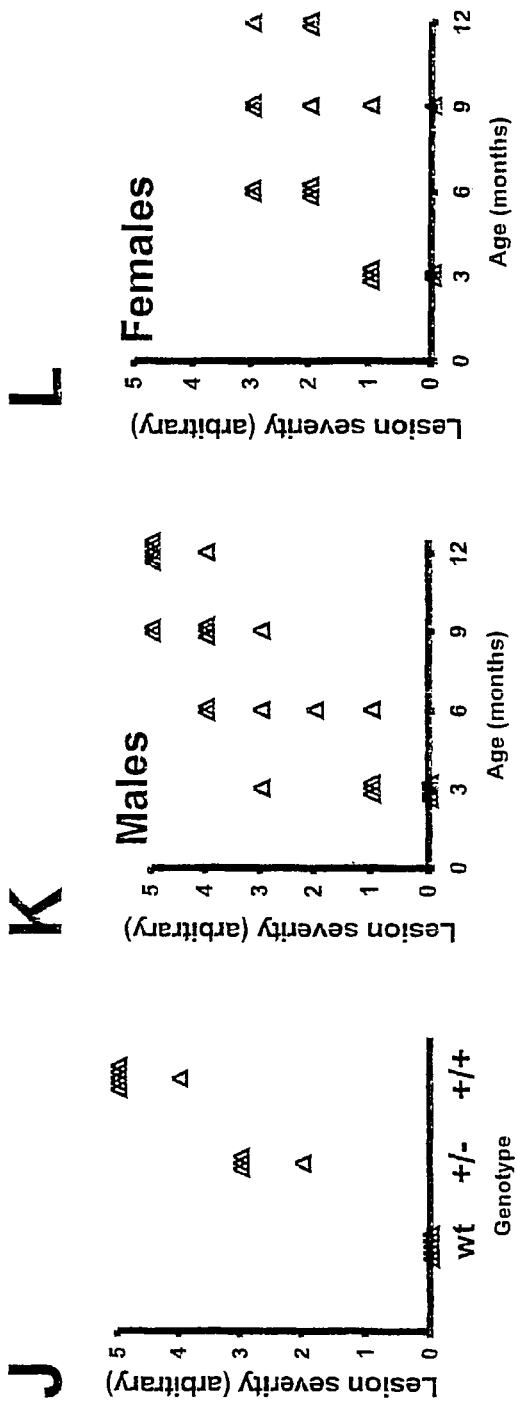

The present inventors also detected glands in the subserosa that were clearly defined by connective tissue and associated with lymphatic tissue, vessels, fat and sometimes nerves (FIG. 3I), indicative of a severe perturbation of the differentiation status of these tissues. These alterations are characteristic for hamartomas of the human stomach. Intestinal metaplasia was common in most cysts of the tumours demonstrating staining of intestinal-type mucous not normally observed in the corpus of the stomach (FIGS. 4A–B). Moreover, squamous metaplasia resulting in formation of squamous cysts was also observed (data not shown). A closer analysis of the expansively growing epithelial cells penetrating the muscularis mucosa layer showed that these cells were not surrounded by cells of the muscularis mucosa layer (FIGS. 4C–D). This observation rules out herniation as the cause of penetration, consistent with an invasive growth behaviour. The present inventors also detected squamous cysts that were focally located on the caecum and occasionally on the ileum in several CA-AhR mice six months of age or older (FIGS. 4E–F). Although the CA-AhR was expressed at the highest level in the glandular part of the stomach with a resulting strong CYP1A1 induction response, the transgene was expressed and functionally active throughout the entire gastrointestinal tract (FIG. 4G). Despite this fact no other major lesions than those described were found in the gastrointestinal tract.

The gastric tumours were not found in any wild type mice (n>200) but in more than 200 transgenic animals. Moreover, the tumours appeared in three independent lines of CA-AhR mice, indicating that the neoplasia was not an effect of random integration of the expression construct into the genome. Heterozygous mice showed less severe stomach tumours than homozygous mice, indicating a gene-dosage effect (data not shown). Moreover, the severity of the gastric tumours increased with age, and males were more severely affected (data not shown), further illustrating the sex difference in susceptibility to the CA-AhR, previously observed with regard to mortality (FIG. 2C).

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

REFERENCES

1. Gu, Y. Z., Hogenesch, J. B. & Bradfield, C. A. (2000) *Annu. Rev. Pharmacol.Toxicol.* 40, 519–561.
2. IARC (1997) *IARC Monogr. Eval. Carcinog. Risks Hum.* 69, 33–343.
3. Shimizu, Y., Nakatsuru, Y., Ichinose, M., Takahashi, Y., Kume, H., Mimura, J., Fujii-Kuriyama, Y. & Ishikawa, T. (2000) *Proc. Natl. Acad. Sci. USA* 97, 779–782.
4. Lahvis, G. P. & Bradfield, C. A. (1998) *Biochem. Pharmacol.* 56, 781–787.

5. Mimura, J., Yamashita, K., Nakamura, K., Morita, M., Takagi, T. N., Nakao, K., Ema, M., Sogawa, K., Yasuda, M., Katsuki, M. & Fujii-Kuriyama, Y. (1997) *Genes Cells* 2, 645–654.
6. Lahvis, G. P., Lindell, S. L., Thomas, R. S., McCuskey, R. S., Murphy, C., Glover, E., Bentz, M., Soutard, J. & Bradfield, C. A. (2000) *Proc. Natl. Acad. Sci. USA* 97, 10442–10447.
7. Fernandez-Salguero, P. M., Ward, J. M., Sundberg, J. P. & Gonzalez, F. J. (1997) *Vet. Pathol.* 34, 605–614.
8. Whitelaw, M. L., Gustafsson, J. Å. & Poellinger, L. (1994) *Mol. Cell. Biol.* 14, 8343–8355.
9. Bodrug, S. E., Warner, B. J., Bath, M. L., Lindeman, G. J., Harris, A. W. & Adams, J. M. (1994) *EMBO J.* 13, 2124–2130.
10. Sambrook, J., Fritsch, E. F. & Maniatis, T. (1989) *Molecular cloning: A Laboratory Manual* (Cold Spring Harbour Laboratory Press, Cold Spring Harbour, N.Y.).
11. Gradin, K., Toftgård, R., Poellinger, L. & Berghard, A. (1999) *J. Biol. Chem.*274, 13511–13518.
12. Mangelsdorf, D. J. & Evans, R. M. (1995) *Cell* 83, 841–850.
13. Whitelaw, M. L., Göttlicher, M., Gustafsson, J. Å. & Poellinger, L. (1993) *EMBO J.* 12, 4169–4179.
14. Jenuwein, T. & Grosschedl, R. (1991) *Genes. Dev.* 5, 932–943.
15. Pohjanvirta, R. & Tuomisto, J. (1994) *Pharmacol. Rev.* 46, 483–549.
16. Gehrs, B. C., Riddle, M. M., Williams, W. C. & Smialowicz, R. J. (1997) *Toxicology* 122, 229–240.
17. Stemmermann, G. N. (1994) *Cancer* 74, 556–564.
18. Endoh, Y., Tamura, G., Motoyama, T., Ajioka, Y. & Watanabe, H. (1999) *Hum. Pathol.* 30, 826–832.
19. Gillner, M., Bergman, J., Cambillau, C., Alexandersson, M., Fernström, B. & Gustafsson, J. Å. (1993) *Mol Pharmacol* 44, 336–345.
20. Kleman, M. I., Övervik, E., Mason, G. G. & Gustafsson, J. Å. (1992) *Carcinogenesis* 13, 1619–1624.
21. Parkin, D. M., Pisani, P. & Ferlay, J. (1999) *Int. J. Cancer* 80, 827–841.
22. Stadtländner, C. T. & Waterbor, J. W. (1999) *Carcinogenesis* 20, 2195–2208.
23. Ekström, A. M., Eriksson, M., Hansson, L. E., Lindgren, A., Signorello, L. B., Nyren, O. & Hardell, L. (1999) *Cancer Res.* 59, 5932–5937.
24. Svensson, B. G., Mikoczy, Z., Stromberg, U. & Hagmar, L. (1995) *Scand. J. Work. Environ. Health* 21, 106–115.
25. Jain, S., Maltepe, E., Lu, M. M., Simon, C. & Bradfield, C. A. (1998) *Mech. Dev.* 73, 117–123.
26. Matikainen, T., Perez, G. I., Jurisicova, A., Pru, J. K., Schlezinger, J. J., Ryu, H. Y., Laine, J., Sakai, T., Korsmeyer, S. J., Casper, R. F., Sherr, D. H. & Tilly, J. L. (2001) *Nat Genet* 28, 355–360.
27. Stewart, H. L., Hare, W. V. & Bennett, J. G. (1953) *J. Natl. Cancer Inst.* 14, 105–125.
28. Stewart, H. L., Snell, K. C. & Hare, W. V. (1958) *J. Natl. Cancer Inst.* 21, 999–1019.
29. Allen, J. R. & Norback, D. H. (1973) *Science* 179, 498–499.
30. Morgan, R. W., Ward, J. M. & Hartman, P. E. (1981) *Cancer Res.* 41, 5052–5059.
31. Milstone, L. M. & LaVigne, J. F. (1984) *J. Invest. Dermatol.* 82, 532–534.
32. Elizondo, G., Fernandez-Salguero, P., Sheikh, M. S., Kim, G. Y., Fornace, A. J., Lee, K. S. & Gonzalez, F. J. (2000) *Mol. Pharmacol.* 57, 1056–1063.
33. Ma, Q. & Whitlock, J. P. (1996) *Mol. Cell. Biol.* 16, 2144–2150.
34. Kolluri, S. K., Weiss, C., Koff, A. & Gottlicher, M. (1999) *Genes. Dev.* 13, 1742–1753.
35. Ceci, J. D., Kovatch, R. M., Swing, D. A., Jones, J. M., Snow, C. M., Rosenberg, M. P., Jenkins, N. A., Copeland, N. G. & Meisler, M. H. (1991) *Oncogene* 6, 323–332.
36. Sandmöller, A., Halter, R., Gomez-La-Hoz, E., Gröne, H. J., Suske, G., Paul, D. & Beato, M. (1994) *Oncogene* 9, 2805–2815.
37. Thompson, J., Epting, T., Schwarzkopf, G., Singhofen, A., Eades-Perner, A. M., van Der Putten, H. & Zimmermann, W. (2000) *Int. J. Cancer* 86, 863–869.
38. Searle, P. F., Thomas, D. P., Faulkner, K. B. & Tinsley, J. M. (1994) *J. Gen. Virol.* 75, 1125–1137.
39. Ge, N. L. & Elferink, C. J. (1998) *J. Biol. Chem.* 273, 22708–22713.
40. Puga, A., Barnes, S. J., Dalton, T. P., Chang, C., Knudsen, E. S. & Maier, M. A. (2000) *J. Biol. Chem.* 275, 2943–2950.
41. Sharp, R., Babyatsky, M. W., Takagi, H., Tagerud, S., Wang, T. C., Bockman, D. E., Brand, S. J. & Merlino, G. (1995) *Development* 121, 149–161.
42. Strayer, D. S., Yang, S. & Schwartz, M. S. (1993) *Lab. Invest.* 69, 660–673.
43. Gaido, K. W., Maness, S. C., Leonard, L. S. & Greenlee, W. F. (1992) *J. Biol. Chem.* 267, 24591–24595.

The invention claimed is:

1. A transgenic mouse whose genome comprises a transgene encoding a constitutively active hydrocarbon receptor (CA-AhR), wherein the CA-AhR is the mouse AhR sequence lacking amino acids 288–421, operably linked to a SV40 promoter and wherein expression of the transgene results in the phenotype of gastric tumors in said mouse.

2. An isolated cell of the transgenic mouse of claim 1, wherein the cell expresses CA-AhR.

3. An isolated cell line derived from the transgenic mouse of claim 1, wherein the cells express CA-AhR.

4. The cell of claim 2, wherein said cell is selected from a germ cell or a somatic cell.

5. A method of producing the transgenic mouse of claim 1, comprising:
   i) introducing a transgene encoding a constitutively active hydrocarbon receptor (CA-AhR), wherein the CA-AhR is the mouse AhR sequence lacking amino acids 288–421, operably linked to a SV40 promoter into a fertilized mouse egg,
   ii) permitting the egg to develop into a mouse whose genome comprises said transgene, wherein the mouse exhibits the phenotype of gastric tumors.

* * * * *